United States Patent [19]

Jinotti

[11] Patent Number: 4,995,387
[45] Date of Patent: Feb. 26, 1991

[54] DUAL-PURPOSE CATHETER

[76] Inventor: Walter J. Jinotti, 10 Scott St., New Brunswick, N.J. 08903

[21] Appl. No.: 270,057

[22] Filed: Nov. 14, 1988

Related U.S. Application Data

[63] Continuation of Ser. No. 871,789, Jun. 9, 1986, abandoned, which is a continuation-in-part of Ser. No. 577,986, Jul. 8, 1984, abandoned.

[51] Int. Cl.$^5$ ............................................. A62B 9/02
[52] U.S. Cl. ............................. 128/205.24; 128/912
[58] Field of Search ............... 128/207.14, 207.15, 128/207.16, 205.24, 912, 205.19, 202.27; 604/43–45, 118, 119, 174

[56] References Cited

U.S. PATENT DOCUMENTS

| 2,667,682 | 2/1954 | Stone | 604/45 |
| 3,114,373 | 12/1963 | Andersen | 604/45 |
| 4,036,210 | 7/1977 | Campbell et al. | 128/207.16 |
| 4,193,406 | 3/1980 | Jinotti | 128/205.19 |
| 4,300,550 | 11/1981 | Gandi et al. | 128/207.18 |

Primary Examiner—Max Hindenburg
Assistant Examiner—John P. Lacyk
Attorney, Agent, or Firm—Robert A. Green

[57] ABSTRACT

A two-tube dual purpose catheter comprising two flexible tubes, an oxygen tube and a suction tube secured together by a rupturable bridging member, the two tubes having different diameters. An adapter is also provided for coupling the two tubes to means for providing oxygen or suction to a patient.

20 Claims, 4 Drawing Sheets

DUAL-PURPOSE CATHETER

This application is a division of application Ser. No. 06/871,789 filed June 9, 1986 now abandoned which is a continuation-in-part of application Ser. No. 06/577,986 filed July 8, 1984 now abandoned.

BACKGROUND OF THE INVENTION

The present invention relates to a catheter which can be inserted in the body and can provide suction or oxygen as desired by the operator of the catheter. U.S. Pat. No. 4,193,406 of Walter J. Jinotti shows one form of suction oxygen catheter which operates satisfactorily; however, the apparatus shown does not readily lend itself to mass production and is larger than is desired. It is also somewhat inconvenient to operate the catheter to switch from suction operation to oxygen feed.

The present invention provides a suction-oxygen catheter which is small, easy to assemble and operate, and is easy to mass produce.

DESCRIPTION OF THE DRAWINGS

FIG. 3 is a side elevational view of one portion of the invention;

FIG. 4 is a side elevational view of another portion of the invention;

FIG. 6 is a sectional view of flexible tubing used with the catheter of the invention.

DESCRIPTION OF THE INVENTION

Figure 1:
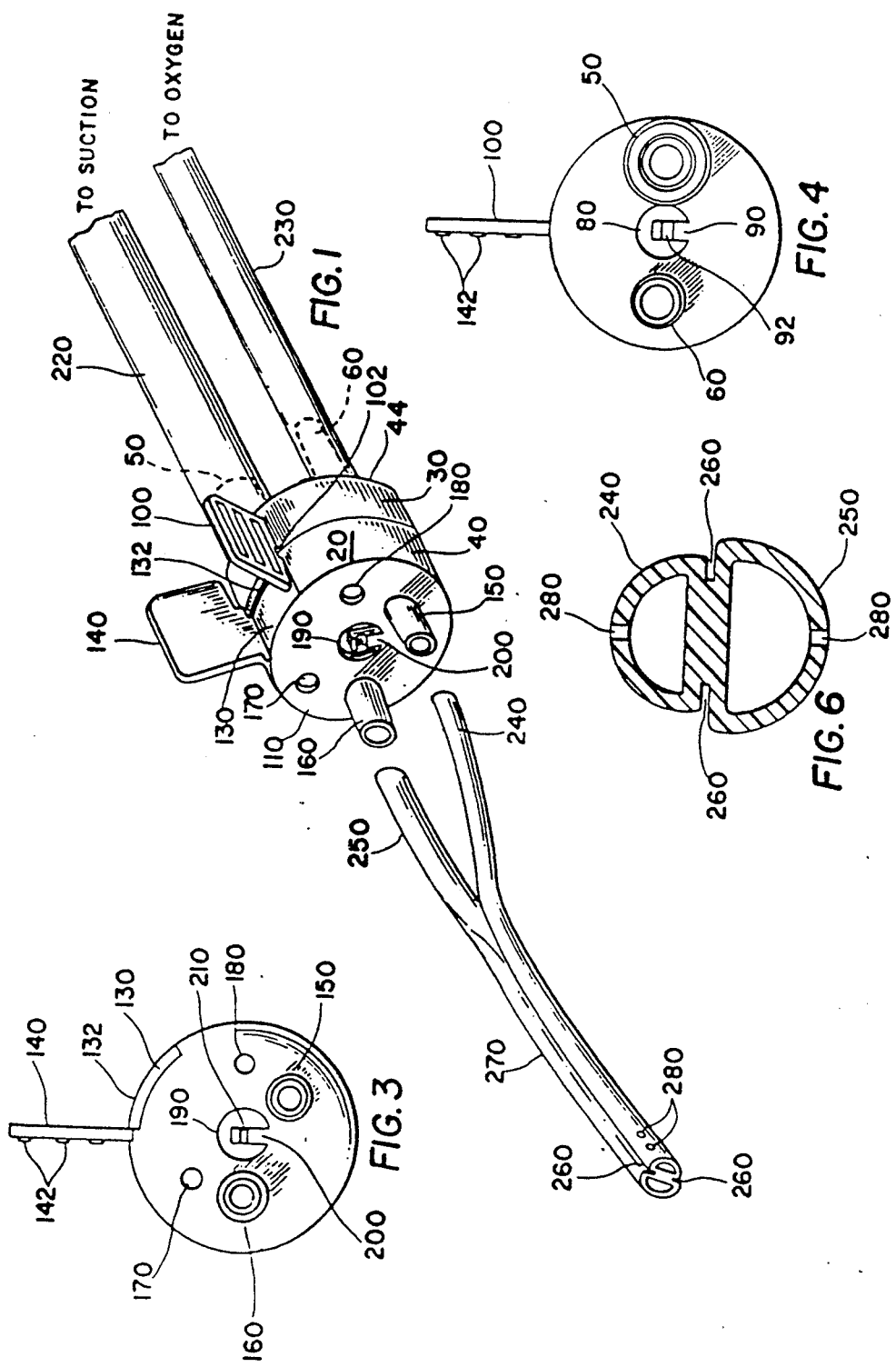
FIG. 1 is a perspective view of the catheter of the invention.

The dual purpose catheter of the invention 10 includes a valve control mechanism 20 of a synthetic resinous material comprising two bodies 30 and 40 having circular cross-sections and rotatably coupled together. One body 30 includes a flat rear wall 44, through which first and second integral tubes 50 and 60 extend so that the two tubes lie inside and outside the body and thus inside the valve mechanism. The inner ends 51 and 61 of tubes 50 and 60 are as smooth as possible for a purpose to be described. Tube 50 is used for connection to a suction source, and tube 60 for connection to an oxygen supply, and the suction tube 50 is preferably of larger diameter. A portion 70 of the inner wall of the body 30 (FIG. 2) near rear wall 44 is thickened or is of reduced inside diameter to provide an annular ledge 74 which acts as a stop for the leading end of body 40 when the two are assembled. The rear wall 44 of the body 30 also has a central hole 80 and a notched tab 90 which is formed integral with the body 30 and extends partly across the hole 80. The tab 90 has notch or depression 92 across its outer surface.

An operating finger tab 100 extends generally perpendicularly from the outer surface of the body 30 for manipulation by the operator of the catheter. The lower edge of tab 100 has a notch 102 for a purpose to be described.

The second body 40 includes a rear wall 110, whose inner surface 112 is as smooth as possible, for a purpose to be described. The annular outer wall 120 of body 40 has a portion 122 of reduced thickness or smaller outside diameter at its leading end for insertion into body 30. Also, the outer surface of the thicker portion 124 is provided with a region 130 of reduced thickness (FIG. 1) having a ledge 132 (FIGS. 1 and 2) where it joins the portion 122 of reduced thickness. An integral operating finger tab 140 extends generally perpendicularly from the thicker annular wall portion at one end of the portion 130 of reduced thickness.

Figure 2:
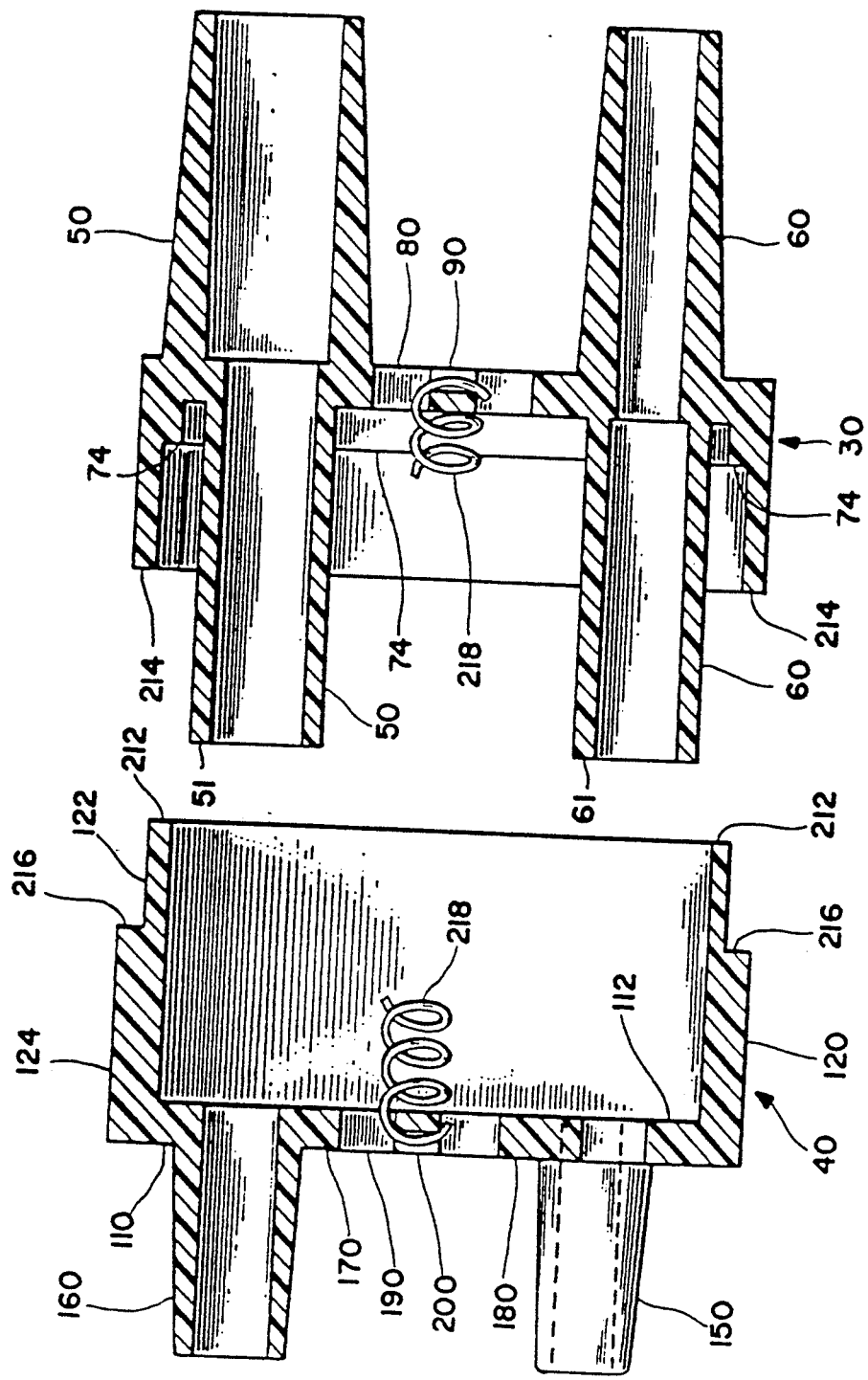
FIG. 2 is a sectional exploded view of the invention.

The finger tabs 100 and 140 are provided with roughened strips 142 on their outer opposite faces, shown only in FIGS. 2, 3, and 4, to facilitate their manipulation by the user of the catheter.

Two tubes 150 and 160 extend away from the wall 110, one 150 for oxygen and one 160 for suction. The two tubes 150 and 160 communicate with the inside of the body 40 through holes 152 and 162 in the rear wall 110. The rear wall 110 also has two holes 170 and 180 located on the same circumference as the two tubes 150 and 160, and a central opening 190. A small integral tab 200 having a notch 210 extends part way across the opening 190.

When the two bodies 30 and 40 are put together, the thin annular wall 122 of the body 40 fits snugly into the opening in body 30, and the leading end 212 butts up against the ledge 74. Similarly, the leading end 214 of body 30 butts up against ledge 216 where wall 122 meets wall 124 of the body 40. Also, the inner ends 51 and 61 of tubes 50 and 60 form a tight fit against the inner surface 112 of rear wall 110 of body 40 to provide an essentially leak-proof coupling between body 30 and body 40. When the bodies 30 and 40 are put together, the finger tab 100 slips over the rim 132, and the notch 102 in the lower surface thereof engages and locks in on the rim.

The two bodies 30 and 40 are held together securely and tightly by means of a helical spring 218 which is secured at its ends in the notches 92 and 210 in the tabs 90 and 200. In attaching the spring 218, with the two bodies 30 and 40 loosely coupled together, one end of the spring is shaped like a hook and is secured to notch 92, and, with the other end grasped by a hooked instrument, the spring is rotated to bias it, and then its other end, which is also shaped like a hook, is set in notch 210 in tab 200, and the bodies are locked together. The spring holds bodies 30 and 40 tightly together with the inner portions 51 and 61 of tubes 50 and 60 snug against the inner surface 112 of end wall 110. The bias set into the spring serves to keep the bodies 30 and 40 rotated so that the finger tabs 100 and 140 are at their maximum distance, apart. With this orientation of the bodies, the oxygen tube 60 is aligned with the oxygen feed tube 150 through its hole 152 in wall 110, and the suction tube 50 is aligned with hole 170 and the ambient atmosphere. When the tabs 100 and 140 are squeezed together, the suction tube 50 is aligned with suction tube 160 through its hole 162 in the wall 110, and the oxygen tube 60 is aligned with the hole 180 and the ambient atmosphere.

The tube 50 is connected by flexible plastic tubing 220 to a source of suction (not shown), and the tube 60 is similarly connected by tubing 230 to an oxygen source (not shown).

According to the invention, the oxygen and suction tubes 150 and 160, the patient side of the valve mechanism, are connected to plastic tubes 240 and 250, respectively, which are threaded over the tubes 150 and 160 or are inserted into the tubes and are cemented therein. The oxygen tube 240 is of smaller diameter than the suction tube 250. The tubes 240 and 250 are manufactured as an integral unit, and they preferably have generally semicircular cross-sections with the flat portions of the tubes adjacent to each other (FIG. 6). The tubes 240 and 250 are separated a small amount, at one end, to permit them to be secured to tubes 150 and 160. The unitary assembly of plastic tubes 240 and 250 is provided with well-defined grooves 260 between them (FIGS. 1 and 6). The tube assembly also preferably has a curvature 270 built into it when it is manufactured. The patient end of the oxygen and suction tubes also have several small holes 280 at their ends to assist them in performing their functions.

When the catheter 10 is used, both the built-in curvature 270 of the assembly of tubes 240 and 250 and the difference in the diameters of the tubes combine to impart controllability of the assembly by the operator, and permit easy guidance of the patient ends of the tubes into the throat and into the left or right lung. In addition, as the tubing is moved and rotated, the grooves 260 in the tubing act as a rake and loosen mucus which can be removed by the suction.

In using the apparatus, the finger tabs 100 and 140 and all of the parts are set so that suction force passes from the tube 250 and tube 160 through the valve 20 and out through the tube 220. At this time, oxygen flows through tubing 230 and tube 60 and out of the hole 180 to the atmosphere. After a suitable time interval of suctioning, the tabs 100 and 140 are pressed together to align the oxygen tubes 60 and 150 and to align the suction tube 50 with the hole 170 to the atmosphere, and oxygen is administered. After a while, the tabs are manipulated and oxygen is discontinued, and suction is applied.

Figure 5:
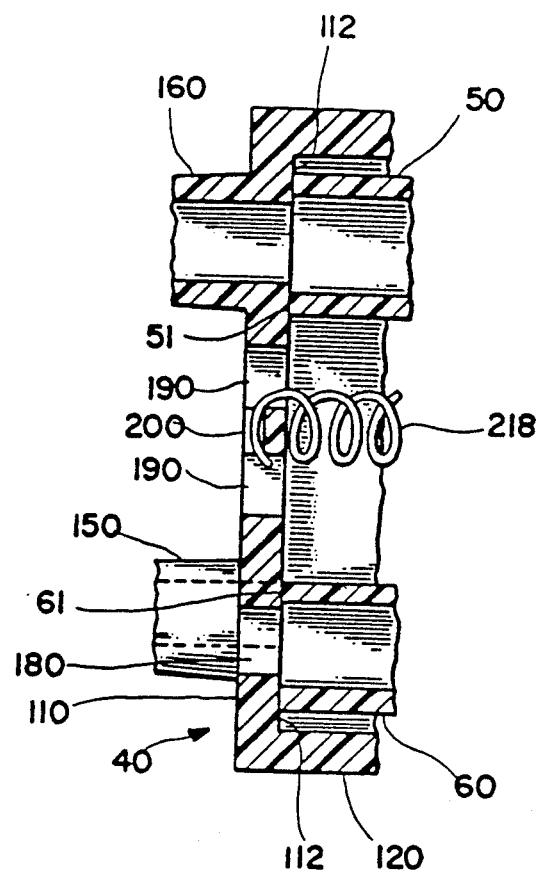
FIG. 5 is a sectional view of a portion of the catheter of the invention showing the relationship of certain parts when the catheter is assembled.

It should be understood that the drawings, and especially FIGS. 2 and 5, are drawn, in general, to make the invention clear, not to be dimensionally correct and not to show all of the parts in their exact location.

Figure 7:
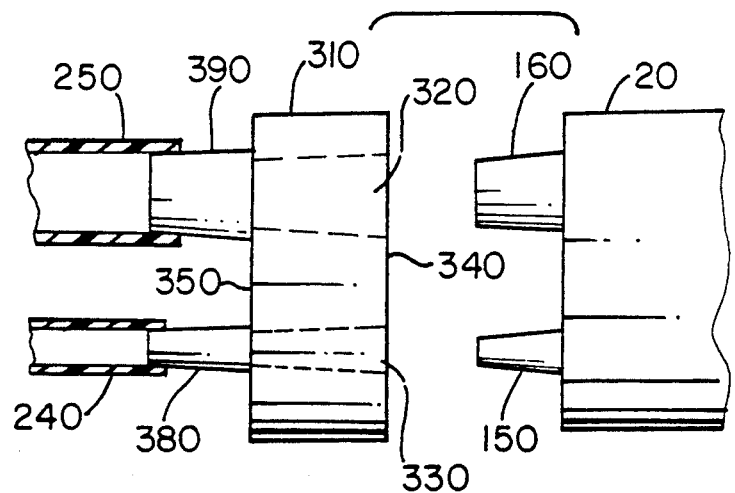

In a modification of the invention, shown in FIG. 7, a two-tube catheter assembly uses an adapter or coupler or coupling member 310 to couple the patient tubes 240 and 250 to the valve mechanism 20 to insure proper connection of the oxygen tube to the oxygen line and the suction tube to the suction line. In this embodiment of the invention, the adapter 310 comprises a rigid plastic body having two through holes 320 and 330 and a front surface 340 and a rear surface 350. The holes 320 and 330 are shaped and dimensioned so that when the adapter is coupled to the patient end of the valve mechanism, hole 320 forms a tight fit with tube 160 and hole 330 forms a tight fit with tube 150.

The surface 350 of the adapter 310 has a small projecting tube 380 to which the small diameter patient oxygen tube 240 can be secured and a larger-diameter projecting tube 390 to which the large-diameter patient suction tube 250 can be coupled. If desired, the rear surface of the adapter may have two holes rather than tubes 380 and 390 in which the ends of the oxygen and suction tubes can be secured directly. In addition at the front surface, holes 320 and 330 may have external tubes to fit over or into tubes 250 and 160 of valve 20.

The use of adapter 310 insures proper and correct and easy coupling of the patient tubes to the valve mechanism 20 and insures that the correct treatment will be provided to the patient at all times and accidental reversing of the oxygen and suction functions cannot occur.

Since the body of the adapter 310 is rigid, the two tubes 380 and 390 are always spaced apart the same fixed distance and this feature along with the difference in diameters of the two tubes insures that the adapter, carrying the two-tube catheter can only be connected one way, the correct way, to the valve 20. The tubes 380 and 390 might also be other than circular and might have key arrangements if desired.

Figure 8:
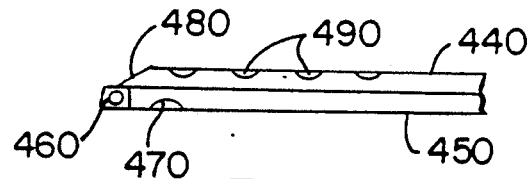

In one form of the two-tube catheter assembly of the invention, shown in FIG. 8, a suction tube 450 is open at its patient end 460 and has at least two suction holes 470 spaced apart along its length. The oxygen tube 440 is open at its patient end 480 which lies close to the end of the suction tube. The oxygen tube also has a plurality of holes 490 along its length.

Figure 9:
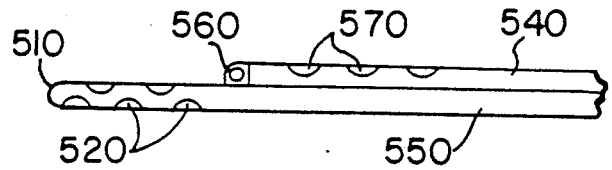

In still another modification of the two-tube catheter assembly shown in FIG. 9, and this is particularly useful as a pediatric catheter, the assembly includes a large-diameter suction tube 500 having a rounded, closed patient end 510 and many holes 520, more than in the adult catheter, in its wall along its length rearwardly of the patient end. The oxygen tube 540 has an open patient end 560 and a plurality of holes 520 along its wall. The open end 560 lies back about one inch from the end of the suction tube to separate their actions. The suction tube having a closed end and holes along its wall sucks mucus from along the wall of the patient's air passages and does not apply suction force to the lungs, a potentially dangerous occurrence in a child.

Figure 10:
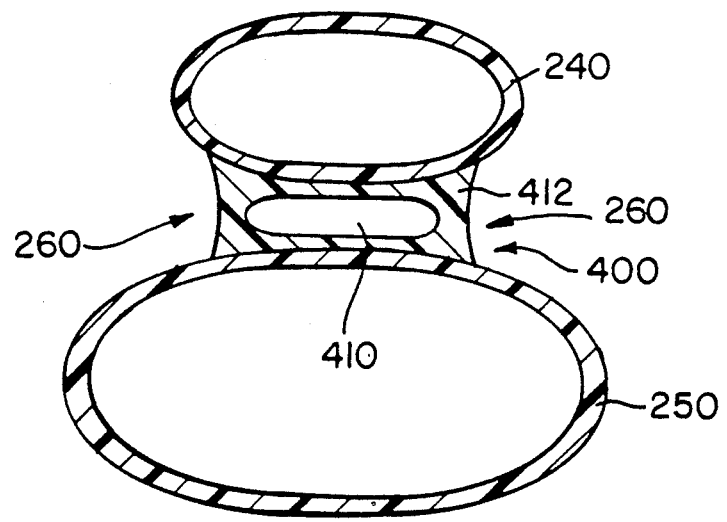

According to another aspect of the invention illustrated in FIG. 10, the two-tube catheter assembly is manufactured as a continuous structure of the oxygen tube 240 and the suction tube 250 having different diameters and coupled together along their entire lengths by a bridging or coupling strip 400 which lies between the two tubes and extends along the lengths thereof. The bridge 400 essentially lies along the adjacent diameters of the two tubes when they are semicircular in cross section. However, the bridge is not as wide as the two tubes so that the relatively deep groove 260 is formed and runs along opposite sides of the bridge. According to the invention, the coupling bridge, which is of a plastic like the two tubes, has an air space or hollow 410 present either along its entire length or at the ends which are to be coupled to the valve mechanism. At this end the tubes must be spread apart so that they can be connected to the valve mechanism or to the adapter 310 and the hollow space or air space 410 leaves only a small amount of bridge material 412 on the sides of the air space to be ruptured to separate the two tubes.

I claim:

1. A dual purpose catheter assembly comprising
a first flexible tube,
a second flexible tube,
one of said tubes being used to supply oxygen to a patient and the other of said tubes being used to apply suction to a patient,
each of said tubes having a patient end and a second end, both said second ends being adapted to be connected to valve means for controlling the alternate providing of oxygen and suction to a patient, and
a rigid unitary coupling member adapted to couple said first and second tubes to valve means for supplying oxygen and suction, said coupling member being secured to said second end of each of said first and second flexible tubes to form a unitary assembly of said coupling member and said first and second flexible tubes, said coupling member, carrying said first and second flexible tubes, being adapted to be coupled to valve means for providing oxygen and suction, said rigid coupling member and said first and second ends of said first and second tubes having such configuration that they can be coupled together in only one orientation which, when said rigid coupling member is coupled to valve means for supplying oxygen and suction, insures the correct coupling of oxygen and suction to a patient.

2. The catheter defined in claim 1 wherein said coupling member comprises a single rigid body having two through holes.

3. The catheter defined in claim 1 wherein said coupling member comprises a single rigid body having two through holes and means for connecting said first tube to one of said holes and said second tube to the other of said holes.

4. The catheter assembly defined in claim 1 wherein said first and second ends of said first and second tubes have different diameters and said coupling member has through-holes of different diameters whereby each through-hole can be coupled only to one of said first and second tubes.

5. The catheter defined in claim 4 wherein said coupling member includes two projecting tubes, each aligned with one of said through holes, said two projecting tubes being adapted to be connected to said other ends of said first and second tubes.

6. The catheter defined in claim 5 wherein said other ends of said first and second tubes have different diameters and said two projecting tubes in said coupling member have different diameters whereby each projecting tube can be coupled only to one of said first and second tubes.

7. The catheter defined in claim 1 wherein said first tube is adapted to operate as a suction tube and has a patient end which is closed and rounded, and a plurality of holes in the wall of said first tube near the patient end thereof, said second tube being adapted to operate as an oxygen tube, the patient end of said second tube being spaced from the patient end of said first tube, said first and second tubes being secured together at their patient ends.

8. The catheter defined in claim 1 wherein said coupling member includes two projecting tubes which are aligned with through-holes therethrough and are dimensional to form a tight fit with said first and second tubes.

9. The catheter defined in claim 8 wherein said two projecting tubes are shaped so that each can fit only one of said first and second tubes.

10. The catheter defined in claim 9 wherein said two projecting tubes are secured to one end of said through hole and the other end of each through hole is coupled to a valve having means for providing oxygen to said oxygen tube and suction to said suction tube.

11. The catheter defined in claim 10 wherein said through holes are shaped so that they can be coupled only to the correct portion of said valve.

12. The catheter defined in claim 8 wherein said two projecting tubes are spaced apart a fixed distance.

13. A dual purpose catheter assembly comprising
a first flexible tube,
a second flexible tube,
one of said tubes being used to supply oxygen to a patient and the other of said tubes being used to apply suction to a patient,
a valve body including a first surface having first means for providing oxygen and suction to said first and second tubes and a second surface having second means for connection to a source of oxygen and a source of suction,
each of said tubes having a patient end for insertion into a patient and a second end adapted to be coupled to said valve body, said valve body controlling the alternate provision of oxygen and suction to a patient, and
a rigid, unitary coupling member secured to said second end of each of said first and second tubes to form a unitary assembly of said coupling member and said first and second tubes, said coupling member and said first and second tubes carried thereby being adapted to be coupled to said first surface of said valve body,
said rigid coupling member having structural means for connection to said first means on said first surface,
said structural means and said first means having such configuration that they can be coupled together in only one orientation which insures that the tube for feeding oxygen is correctly coupled to the source of oxygen and the tube for applying suction is correctly connected to the source of suction.

14. The assembly defined in claim 13 wherein said structural means on said rigid coupling member and said first means on said valve body are so shaped that they can be connected to each other in only one orientation to insure correct treatment of the patient.

15. The assembly defined in claim 13 wherein said first means on said valve body are tubes of different diameters.

16. The assembly defined in claim 15 wherein said first means on said valve body have corresponding different diameters.

17. The assembly defined in claim 15 wherein said tubes are non-circular in structure and said first means on said coupling member are correspondingly non-circular.

18. The assembly defined in claim 15 wherein said structural means on said coupling member are through holes having different diameters generally the same as the diameters of said tubes so that correct coupling can occur automatically.

19. The assembly defined in claim 17 and said structural means on said coupling member are through holes having non-circular form to match the non-circular form of said tubes so that only correct coupling of said coupling member and said valve body can occur.

20. The assembly defined in claim 19 wherein said tubes on said valve body are semi-circular in shape and said through-holes in said coupling member are correspondingly semi-circular in shape.

* * * * *